United States Patent [19]

Liang et al.

[11] Patent Number: 5,614,644
[45] Date of Patent: Mar. 25, 1997

[54] PROCESS FOR THE REMOVAL OF ORGANIC CHLORIDES FROM FURAN AND HYDROGENATED FURANS

[75] Inventors: Shaowo Liang; John R. Monnier; Stanley J. Okrasinski, all of Kingsport; Timothy W. Price, Church Hill, all of Tenn.

[73] Assignee: Eastman Chemical Company, Kingsport, Tenn.

[21] Appl. No.: 521,933

[22] Filed: Sep. 1, 1995

[51] Int. Cl.$^6$ .................. C07D 307/06; C07D 307/08; C07D 307/28; C07D 307/36
[52] U.S. Cl. ................... 549/507; 549/429; 549/505
[58] Field of Search .......................... 549/507, 505, 549/429

[56] References Cited

U.S. PATENT DOCUMENTS 3,163,660  12/1964  Strohmeyer et al. ............... 549/507
3,883,566   5/1975  Johnson et al. .................... 549/529
4,233,228  11/1980  Mueller et al. .................... 549/529
4,774,347   9/1988  Marko et al. .
5,399,752   3/1995  Okrasinski et al. .

FOREIGN PATENT DOCUMENTS 576553  4/1946  United Kingdom ................ 549/507

OTHER PUBLICATIONS

Berty et al. (Stud. Surf. Sci. Catal. 1993,75, pp. 1571–1574).
Vlasenko et al. (Khim. Prom–st. 1989, pp. 739–741).

*Primary Examiner*—Joseph E. Evans
*Attorney, Agent, or Firm*—J. Frederick Thomsen; Harry J. Gwinnell

[57] ABSTRACT

Disclosed is a process for the removal of organic chlorides from furan and hydrogenated furans by contacting a crude product stream comprising (i) furan, 2,3-DHF, 2,5-DHF, THF or a mixture thereof and (ii) one or more organic chlorides with a copper-containing scavenger material.

3 Claims, No Drawings

PROCESS FOR THE REMOVAL OF ORGANIC CHLORIDES FROM FURAN AND HYDROGENATED FURANS

This invention pertains to a process for the removal of organic chlorides from furan and hydrogenated furans. More specifically, this invention pertains to a process for the removal of organic chlorides from, 2,3-dihydrofuran (2,3-DHF), 2,5-dihydrofuran (2,5-DHF) and tetrahydrofuran (THF) by contacting the material containing one or more organic chlorides with a copper-containing, chloride scavenger material.

U.S. Pat. No. 4,897,498 describes an efficient process for the preparation of conjugated epoxyalkenes by the selective monoepoxidation of dienes, e.g., 3,4-epoxy-1-butene from 1,3-butadiene. Many valuable compounds can be derived from 3,4-epoxy-1-butene. Processes for the isomerization or rearrangement of 3,4-epoxy-1-butene to 2,5-DHF are described in U.S. Pat. Nos. 3,932,468, 3,996,248 and 5,082,956. A process for the isomerization of 2,5-DHF to 2,3-DHF is described in U.S. Pat. No. 5,254,701. THF is obtained easily by the hydrogenation of either 2,5-DHF or 2,3-DHF.

In the monoepoxidation of butadiene to 3,4-epoxy-1-butene using a modified silver catalyst, one or more organic chlorides commonly are used to improve the selectivity of the epoxidation process. See, for example, U.S. Pat. No. 4,950,773. In spite of the efficiency of most separation methods, however, most of the organic chlorides (for example, 2-chlorobutane) used in the monoepoxidation of butadiene is passed on to the downstream products 2,5-DHF, 2,3-DHF, THF and furan in concentrations of up to 1500 parts per million by volume (ppmV). It is understood by those experienced in the art that ppmV of gas phase compositions is the same as parts per million Molar and that these two terms, ppmV and ppm Molar, are often used interchangeably. The problem of contamination of these furan and hydrogenated furans by organic chlorides is complicated by the fact that many organic chlorides, particularly alkyl chlorides such as 2-chlorobutane, are difficult or impossible to remove from the hydrogenated furans by conventional separation procedures, such as fractional distillation, because of the similarity of the boiling points of the alkyl chlorides (2-chlorobutane b.p.=68° C.) and 2,5-DHF (b.p.=67° C.), THF (b.p.=67° C.) and 2,3-DHF (b.p.=55° C.). The possible existence of one or more constant boiling mixtures (azeotropes) may be another reason. Organic chlorides can cause serious problems in manufacturing applications due to their thermal instability, potentially decomposing into olefin and hydrogen chloride. For certain end uses of these furan and hydrogenated furans, it is required that the organic chloride content be below 5 parts (ppmV).

U.S. Pat. No. 4,774,347 describes a process for the removal of organic chlorides from crude alkylsilanes by converting an organic chloride impurity to saturated hydrocarbons and more highly chlorinated alkylsilanes in the presence of a hydrogen-containing silane and a Lewis acid, e.g, $AlCl_3$, $CoCl_2$, $ZrCl_2$ and $CuCl_2$. The chlorinated alkylsilanes formed are then separated from alkylsilane by distillation. This process requires a stoichiometric excess of the hydrogen-containing silane relative to the organic chloride impurities. The use of strong Lewis acids is not suitable for the removal of organic chlorides from hydrogenated furans. For example, it is known that 2,3-DHF can rapidly polymerize in the presence of a Lewis acid (D. A. Barr and J. B. Rose, *J. Chem. Soc.* 1954pp 3766–3769).

JP 51-022699 describes a catalytic oxidation process to recover chlorine from chlorine-containing organic compounds or waste gas by contacting the chlorine-containing materials with oxygen and a transition metal oxide catalyst at high temperatures, e.g., 450° C.

Vlasenko et al., (*Khim. Prom-st.* 1989, pp 739–741) describe the removal of ethyl chloride from waste gases by catalytic oxidation using a spinel—type Cu—Co—Cr catalyst. In the presence of oxygen, ethyl chloride is decomposed to hydrogen chloride, carbon dioxide and water.

These processes are not suitable for the removal of organic chlorides in furan and hydrogenated furans. One of the problems with the thermal and catalytic processes described above is the formation of hydrogen chloride. Under the severe conditions required, this free hydrogen chloride can be oxidized to chlorine. Both hydrogen chloride and chlorine can react further with furan and hydrogenated furans. For example, HCl can cause rapid polymerization of 2,3-DHF to give high molecular weight polymers. In addition, the free HCl in the oxidizing environment is very corrosive, requiring expensive materials of construction and a following removal step. Another problem is that oxygen is required in these oxidative processes which will react with the furans to give unwanted combustion products ($CO_2$ and $H_2O$), as well as form peroxides which create serious safety problems in manufacturing.

Berty et al. (*Stud. Surf. Sci. Catal.* 1993, 75, pp 1571–1574) describe a process of oxidation and removal of chlorinated hydrocarbons using copper and manganese catalysts. Again, the presence of oxygen is required for the removal of organic chlorides in the process.

It is known that alkali metals such as lithium or sodium can react with organic chlorides to form chloride salts. However the handling of such metals and the resulting insoluble salts in manufacturing is difficult and also introduces serious concern for safety.

U.S. Pat. No 5,399,752 (and prior art discussed therein) describes a process for the reduction in the iodine content of a crude carboxyl product stream comprising (i) one or more carboxyl compounds selected from carboxylic acids, carboxylic anhydrides and alkylidene dicarboxylates and (ii) iodine, one or more iodine-containing materials or a mixture thereof. The process includes the step of contacting the crude carboxyl stream with a copper-containing scavenger material. The removal of organic chlorides from furan or hydrogenated furans is neither disclosed nor contemplated. U.S. Pat. No. 5,306,398 discloses the use of various metals or metal compounds in conjunction with a basic alkali compound for the purification of a crude acetic acid stream containing both nitrogen and halogen compounds. This complex method is specific to acetic acid streams, requires the use of both metallic and basic compounds and is used in conjunction with two distillation stages.

The process of the present invention represents a highly-efficient means for the removal of organic chlorides from streams that contain furan or hydrogenated furans such as 2,3-DHF, 2,5-DHF and THF. The present invention provides a process for the reduction of chloride content of a crude product stream comprising (i) furan, 2,3-DHF, 2,5-DHF, THF or a mixture thereof and (ii) one or more organic chlorides selected from alkyl chlorides, alkenyl chlorides, cycloalkyl chlorides, aromatic chlorides or a mixture thereof, by the steps of:

(1) contacting the crude product stream, optionally in the presence of an inert gas, with a copper-containing scavenger material in an organic chloride removal zone; and (2) removing from the chloride removal zone a refined product stream containing less chloride than the crude stream. During the operation of the above described process, the passage of the chloride-containing species through the copper-containing scavenging material is believed to result in a chlorine/copper reaction. That is, the copper effectively removes organic chlorides in stoichiometric amounts to form $CuCl_x$, where $0<x<2$. There is no hydrogen chloride generated during the process.

The organic chloride or chlorides are present in the product stream purified according to the invention as a result of being added during the manufacture of 3,4-epoxy-1-butene from which the product stream is derived. See, for example, the organic chlorides described in U.S. Pat. No. 4,950,773. Examples of the organic chlorides which may be present in the crude product stream utilized in the present invention include compounds of the structure $RCl_x$, wherein R is hydrocarbyl radical, e.g., the residue of an alkane, alkene, cycloalkane or carbocyclic aromatic compound containing up to about 8 carbon atoms and x is a value of from 1 to 8, depending, of course, on the hydrocarbyl radical represented by R. Exemplary organic chlorides include $C_1$ compounds such as methyl chloride, methylene chloride, chloroform and the like; $C_2$ compounds such as ethyl chloride, dichloroethane, vinyl chloride, dichloroethylene, trichloroethylene, and the like; $C_3$ compounds such as chloropropane, chloropropene, dichloropropane, dichloropropene and the like; $C_4$ compounds such as chlorobutane, dichlorobutane, chlorobutene, dichlorobutene, trichlorobutane, trichlorobutene and the like; $C_5$ compounds such as mono-, di-, tri-, tetra-, and pentachloro-pentanes or pentenes, cyclopentylchloride and the like; $C_6$ compounds such as mono-, di-, tri-, tetra-, penta- and hexachlorohexanes or hexenes, cyclohexylchloride chlorobenzene and the like; $C_7$ compounds such as mono-, di-, tri-, tetra-, hexa- and heptachloroheptanes or heptenes, chlorocyclohetane and the like; $C_8$ compounds such as mono-, di-, tri-, tetra-, penta- hexa- hepta- and octachlorooctanes or octenes and the like; as well as mixtures of any two or more thereof. The more common organic chlorides comprise the mono- and di-chlorides of alkanes of 2 to 6 carbon atoms, especially the chlorobutanes such as 2-chlorobutane.

The concentration of the organic chloride in the crude product stream may be as high as 5 volume percent but normally is in the range of about 50 to 2000 ppmV (or parts per million Molar). Usually the chloride removal process of the invention will reduce the chloride content of the refined product stream to less than about 15 ppmV, preferably to less than 5 ppmV. The crude product stream which is purified according to the present invention may contain minor amounts, e.g., up to about 15 weight percent, of other impurities such as crotonaldehyde, 3,4-epoxy-1-butene, water, and the like.

The process of this invention may be operated either in the liquid or vapor phase although vapor phase operation is preferred. The temperature and pressure requirements within the organic chloride removal zone may vary substantially depending on numerous factors such as whether the process is operated in the liquid or vapor phase, the particular copper scavenging material employed, the concentration of chloride in the crude furan or hydrogenated furan feed, the degree of purification desired, etc. For example, the process may be carried out at temperatures in the range of about 20°–300° C., more preferably 75°–275° C., and most preferably 100°–260° C. Gradually increasing the temperature in the chloride removal zone during the process is advantageous for maximizing the utility of copper-containing, chloride scavenging materials. The process may be operated at pressures in the range of 0.25 to 10 bars absolute, more preferably in the range of 0.5 to 8 bars absolute, and most preferably in the range of about 1.0 to 5.0 bars absolute. For vapor phase operation the combination of temperature and pressure must be chosen to maintain all components in the vapor phase.

A broad range of copper-containing materials is effective in reducing the concentration of chlorine-containing impurities in accordance with the present invention. The majority of these materials are available commercially as catalysts and are referred to herein as such. The capacity of these materials to remove chloride impurities from process streams depends upon such factors as the amount of copper present on the catalyst, the size of the copper crystallites or aggregates on the support, and the ability to transport the chloride impurities to the active copper surface. The copper-containing materials may be selected from copper sources such as copper gauze packing materials or wire as well as unsupported or supported copper-containing catalysts. Copper chromite is typical of the unsupported catalysts. The supported catalysts comprise copper deposited on a catalyst support material such as alumina, silica, alumina/silica, carbon, titania/silica, titania/alumina, or titania/alumina/silica, preferably silica. The copper content of such supported catalysts may be in the range of about 0.5 to 90 weight percent, more preferably 5 to 75 weight percent and most preferably 10–60 weight percent.

Since copper catalysts generally are received in the oxidized, or air-passivated, form, it is necessary to reduce these materials before use. Reduction, or pre-treatment, most often is accomplished by passing a hydrogen-containing gas over and through the catalyst at temperatures in the range of 200°–275° C. The volume percent of hydrogen in the reducing stream typically is in the range of 5–50% by volume. After this pre-reaction step, the crude product stream, either as a liquid or a vapor, is passed through the chloride removal zone. The flow rates for the crude product stream vapor mixture may be varied substantially and are, in part, determined by the particular copper-containing material used, the surface area and geometric configuration of the copper-containing material and the degree of chloride removal which is desired. Thus, beds of copper catalysts can be simply designed by accepted engineering practices and the scope of the current invention is not to be limited by the particular bed configuration. For vapor phase operation, the flow rate of the crude product stream through the chloride removal zone is given herein as a gas hourly space velocity (GHSV), i.e., unit volume of gaseous crude product stream per hour per unit volume of catalyst. Normally, the GHSV flow rate of the crude product is within the range of about 200 to 20,000, more preferably within the range 300 to 15,000, and most preferably 400 to 10,000. If the chloride removal process is carried out in the liquid phase, the flow rate of the crude product stream is given as liquid hourly space velocity (LHSV), i.e., liquid volume unit of crude product stream flow per hour per volume unit of catalyst. LHSV values for liquid crude product stream may be within the range 0.05 to 50.0, more preferably 0.1 to 20.0, and most preferably 0.2 to 10.0.

After passage through the chloride removal zone, the effluent, whether vapor or liquid, is cooled to allow the collection of the purified product stream comprising furan, 2,3-DHF, 2,5-DHF, THF or a mixture thereof. Alternatively, the effluent may be fed directly to the inlet of a distillation column or other additional purification device or fed directly to a reactor or system in which the effluent can undergo further chemical reactions. For example, after passage through the chloride remove zone, refined 2,3-DHF may be fed directly, without cooling, to a system in which 2,3-DHF is thermally isomerized to cyclopropanecarboxaldehyde, or to a system in which 2,3-DHF undergoes hydration to 2-hydroxytetrahydrofuran which subsequently is hydrogenated to produce 1,4-butanediol. Likewise, after passage through the chloride remove zone, refined 2,5-DHF may be fed directly, without cooling, to a process in which 2,5-DHF is isomerized to 2,3-DHF or hydrogenated to THF.

The present invention is especially useful for the removal of one or more organic chlorides from 2,5-DHF which is destined for isomerization to 2,3-DHF by contacting 2,5-DHF with a supported palladium catalyst at 150° to 170° C. as is described in Auslegeschrift DE 1,248,669. During such a high temperature process, organic halides such as 2-chlorobutane are decomposed to hydrogen chloride and an unsaturated hydrocarbon. The hydrogen chloride formed causes polymerization of the 2,3-DHF product which decreases the yield of 2,3-DHF and can cause fouling of the isomerization equipment. Thus, decreasing the concentration of organic halide in the 2,5-DHF reactant decreases the amount of hydrogen chloride generated which in turn decreases the polymerization of 2,3-DHF.

The process of this invention may be carried out using a gaseous crude product stream feed which contains up to 90 mole, or volume, percent of a inert gas such as nitrogen, helium, argon, carbon dioxide, carbon monoxide, methane, ethane, or the like. The ratio of crude product (furan, 2,3-DHF, 2,5-DHF, THF or a mixture thereof) to such an inert gas may be in the range of about 1.0:0.01 to 1.0:20.0.

Generally, it is advantageous to avoid the introduction of oxygen, or compounds containing reactive oxygen atoms, to the chloride removal zone. The presence of oxygen results in the formation of copper oxide. Small amounts of epoxides such as 3,4-epoxy-1-butene (EpB) in the crude effluent can react with copper to form copper oxide and butadiene which results in decreasing the efficiency of chloride removal. If the concentration of compounds such as EpB in the feed stream is not excessive, the efficiency of the copper-containing scavenger material will not decrease significantly. For example, EpB may be present in concentrations of up to a molar ratio of 0.01 to 0.05 relative to the amount of the crude product stream, i.e., furan, 2,3-DHF, 2,5-DHF, THF or a mixture thereof. However, if the levels of EpB are higher, or if increased efficiency of the copper-containing, chloride removal bed is desired, then the purification process of this invention may be carried out in the presence of carbon monoxide or hydrogen. The purpose of the carbon monoxide or hydrogen is to reduce continuously any copper oxide formed by the reaction with EpB to metallic copper and carbon dioxide or water. The chloride removal process of the present invention preferably is carried out in the absence of molecular oxygen, basic compounds such as alkali metal hydroxides, carbonates, bicarbonates and acetates, and other materials utilized in processes described in the prior art.

The process provided by the present invention is further illustrated by the following examples. Gas chromatographic (GC) analyses were performed on a Hewlett-Packard 5890 series II gas chromatograph with a 50 meter and 0.32 mm id with 1.0 micron film thickness DB-Wax columns. The detection limit for 2-chlorobutane is 0.5 ppmw. The total chlorine analyses were performed on a Philips PW 1400 X-Ray Fluorescence Spectrometer with 5 ppmw detection limit for total chlorine.

The experimental apparatus consisted of a preheater and chloride removal zone containing a solid copper-containing material, a condenser, and a collection flask. The preheater was constructed of a glass tube approximately 33 cm long having an interior diameter of 2.5 cm with a concentric 6 mm diameter thermowell along its length. The preheater was packed with quartz chips and was electrically heated. The purpose of the preheater was to either preheat or to vaporize the crude product stream prior to its entry into the chloride removal zone. The temperature of the preheater was maintained at 75°–100° C. The chloride removal zone was constructed of a glass tube/thermowell assembly having the same dimensions as the preheater. The central 18 cm section of the chloride removal zone assembly contained the copper-containing material being tested. Quartz chips were packed on either side of the copper-containing material, filling the remainder of the glass tube. The assembly was electrically heated and maintained at a predetermined temperature range. The outlet of the chloride removal zone fed into an water-cooled condenser, which allowed the collection of the refined product stream as a liquid. Prior to the commencement of the crude product feed to the apparatus, air was removed from the system by purging with argon. The air removal step was followed by activation of the copper-containing catalyst by a pre-reduction step wherein an 8 to 100 volume percent hydrogen in nitrogen mixture was passed at a rate of 50 mL per minute slightly above 1 atmosphere pressure through the experimental assembly. The initial temperature of the reactor was 200° C. and throughout the activation process a careful watch was maintained to ensure that a reaction exotherm did not raise the temperature of the system to a point which threatened to cause sintering of the catalyst. At no time was the temperature of the chloride removal zone allowed to rise above 300° C. Water was evolved during the activation process giving positive indication that any oxides present on the copper catalysts were being reduced. This pre-activation step was continued for several hours after all signs of water evolution ceased.

CONTROL EXAMPLE 1

Quartz chips (75 mL) were placed within the chloride removal zone and, after assembly, air was removed from the system by purging with argon. Then nitrogen was passed through the bed at 10 mL per minute and the temperature of chloride removal zone maintained at 170° C. A liquid stream of 2,5-DHF containing 148.5 ppmw 2-chlorobutane was then fed at 30 mL (liquid) per hour to the above described apparatus. The liquid stream was vaporized and the vapor stream passed over the heated quartz chips. The effluent vapor stream was cooled and the condensed product was collected. The analysis revealed minimal reduction of 2-chlorobutane as the sample contained almost the same amounts of 2-chlorobutane (144.8 ppmw).

CONTROL EXAMPLE 2

The procedure described in Control Example 1 was repeated except that the temperature of the chloride removal zone was maintained at 140° C. In this instance, the treated 2,5-DHF after condensation was found to contain almost the same amounts of 2-chlorobutane (148.2 ppmw).

EXAMPLE 1

In this example, the chloride removal zone was charged with a copper on silica catalyst (10% copper on silica, Davison #SR167-662, 50 mL) which was activated at 200° C. with hydrogen for 4 hours. After the activation step, nitrogen gas was passed through the bed at 10 mL per minute, the preheater was held constant at 100° C., and the temperature of the chloride removal zone maintained at 110° C. A crude 2,5-DHF stream containing 297.3 ppmw of 2-chlorobutane (total chlorine 123.6 ppmw) was then added to the 10 mL per minute nitrogen flow and then passed through the apparatus at a rate of 120 mL 2,5-DHF (liquid) per hour. The overall gas flow rate was approximately 580 mL per minute and contained approximately 98 mole, or volume, percent 2,5-DHF vapor. The effluent from the chloride removal zone was condensed, collected, and analyzed for 2-chlorobutane (90.2 ppmw) and total chlorine (34 ppmw by X-ray analysis). The removal of 2-chlorobutane was 70% and the recovery of 2,5-DHF was greater than 99%.

EXAMPLE 2

The procedure described in Example 1 was repeated except that the temperature of the chloride removal zone maintained at 120° C. throughout the experiment. In this instance, the treated 2,5-DHF stream was found to contain 25.1 ppmw 2-chlorobutane and 13 ppmw total chlorine. The removal of 2-chlorobutane was 92% and the recovery of 2,5-DHF was 99%.

EXAMPLE 3

The procedure described in Example 1 was repeated except that the temperature of the chloride removal zone maintained at 130° C. throughout the experiment. In this instance, the treated 2,5-DHF stream was found to contain 14.6 ppmw 2-chlorobutane and 7 ppmw total chlorine. The removal of 2-chlorobutane was 95% and the recovery of 2,5-DHF was 99%.

EXAMPLE 4

The procedure described in Example 1 was repeated except that the catalyst was pre-activated at 270° C. for 4 hours prior to use and the temperature of the chloride removal zone was maintained at 150° C. throughout the experiment. A 2,5-DHF stream containing 307.3 ppmw of 2-chlorobutane (total chlorine 126 ppmw by X-ray analysis) was passed through the apparatus at a rate of 30 mL 2,5-DHF (liquid) per hour. In this instance, the treated 2,5-DHF stream was found to contain 6.5 ppmw 2-chlorobutane and less than 5 ppmw total chlorine (below the detection limit of X-ray analysis). The removal of 2-chlorobutane was 98% and the recovery of 2,5-DHF 99%.

EXAMPLE 5

The procedure described in Example 4 was repeated except that the temperature of the chloride removal zone was maintained at 160°C. throughout the experiment. In this instance, the treated 2,5-DHF stream was found to contain 4.0 ppmw 2-chlorobutane and less than 5 ppmw total chlorine (below the detection limit of X-ray analysis). The removal of 2-chlorobutane was 99% and the recovery of 2,5-DHF was 98%.

EXAMPLE 6

The procedure described in Example 4 was repeated except that the temperature of the chloride removal zone was maintained at 170° C. throughout the experiment. In this instance, the treated 2,5-DHF stream was found to contain 3.0 ppmw 2-chlorobutane and less than 5 ppmw total chlorine (below the detection limit of X-ray analysis). The removal of 2-chlorobutane was 99% and the recovery of 2,5-DHF was 98%.

EXAMPLE 7

The procedure described in Example 1 was repeated except that the temperature of the chloride removal zone was maintained at 119° C. throughout the experiment. A 2,3-DHF stream containing 173 ppmw of 2-chlorobutane was passed through the apparatus at a rate of 30 mL 2,3-DHF (liquid) per hour. In this instance, the treated 2,3-DHF stream was found to contain less than 0.5 ppmw 2-chlorobutane (below the detection limit of GC analysis). The removal of 2-chlorobutane was greater than 99% and the recovery of 2,3-DHF was greater than 99%.

EXAMPLE 8

The procedure described in Example 7 was repeated except that the temperature of the chloride removal zone was maintained at 130° C. throughout the experiment. In this instance, the treated 2,3-DHF stream was found to contain less than 0.5 ppmw 2-chlorobutane (below the detection limit of GC analysis). The removal of 2-chlorobutane was greater than 99% and the recovery of 2,3-DHF was greater than 99%.

EXAMPLE 9

The procedure described in Example 1 was repeated except that the temperature of the chloride removal zone was maintained at 100° C. throughout the experiment. A THF stream containing 100 ppmw of 2-chlorobutane was passed through the apparatus at a rate of 30 mL THF (liquid) per hour. In this instance, the purified THF stream was found to contain 0.7 ppmw 2-chlorobutane. The removal of 2-chlorobutane was greater than 99% and the recovery of THF was greater than 99%.

EXAMPLE 10–16

The procedure described in Example 9 was repeated except that the temperature of the chloride removal zone was maintained at 110, 120, 130, 140, 150, 160, and 170° C., respectively. In each of these examples, the treated THF streams was found to contain less than 0.5 ppmw 2-chlorobutane (below the detection limit of GC analysis). The removal of 2-chlorobutane in each experiment was greater than 99% and the recovery of THF was greater than 99%.

EXAMPLE 17

In this example, the chloride scavenging material was 50 weight percent copper on silica catalyst. A sample of the catalyst (2.0 grams, 3.2 mL) which had been sieved to a particle diameter range of 0.084 to 0.188 cm was loaded into a tubular Pyrex glass reactor and placed in a tube furnace. This catalyst was pretreated using the method described in Example 1, whereby the supported copper oxide was reduced to the metallic state. The reduction was performed in situ immediately prior to the 2-chlorobutane removal step. The reactor assembly used for this test utilized an in-line gas sample loop to analyze quantitatively the 2-chlorobutane concentration either above or below the copper catalyst. In this way, it was possible to directly calculate the level of 2-chlorobutane removal from the crude product vapor stream. The crude product stream, in this case 2,5-DHF, was added as a vapor by passing a helium sweep gas flow through a liquid reservoir of 2,5-DHF maintained at a constant temperature. The temperature of the 2,5-DHF typically was maintained at 20° C. to give a gas feed composition of 18% by volume (same as molar for vapor phase compositions) 2,5-DHF in helium. The 2-chlorobutane also was added as a vapor from a liquid reservoir maintained at constant temperature. The temperatures of the reservoir and the helium sweep gas flow rate were selected to give a final composition of between 450–800 ppmV (ppm by volume) of 2-chlorobutane vapor in the 18% 2,5–DHF by volume feed stream. The helium flows were controlled by Tylan FC-260 mass flow controllers to ensure accurate and reliable flow rates. A Hewlett-Packard 5890A gas chromatography using a 25 meter PoraPLOT Q column, film thickness 10 microns, was used to separate the organic products, furan, 2,5-DHF, 2,3--DHF, and THF and the unreacted 2-chlorobutane. The quantities of the organic products were determined using a thermal conductivity detector, while the ppm levels of 2-chlorobutane were determined by a Model 4420, Electrolytic Conductivity Detector (from O. I. Corporation) that was connected in series to the exit of the thermal conductivity detector. Thus, in one analysis it was possible to determine the fate of the 2,5-DHF feed composition and the extent of conversion of ppm levels of 2-chlorobutane. Further, since the in-line gas analysis permitted analysis of the vapor phase composition both above and below the copper catalyst bed, it was possible to calculate very accurately the performance of the copper bed for 2-chlorobutane removal.

As in the case of Control Examples 1 and 2, a 2-chlorobutane removal zone packed with 5 grams of Pyrex glass beads gave no conversion of 2-chlorobutane at temperatures as high as 250° C. Thus, there was no background, or thermal, reaction.

The data in Table I summarize the performance characteristics of the 2.0 gram (3.2 mL) copper on silica catalyst for 2-chlorobutane removal. The data are arranged in the same order as the sequence in which this long term run was conducted. In the Table I, "Temp" is the temperature in ° C. of the catalyst; "GHSV" is the gas hourly space velocity of the gas flow and is determined by dividing the gas hourly flow by the catalyst volume of 3.2 mL;

"Process Time" is the total cumulative time in hours that the chloride removal process had been operating at the time the data listed adjacent to a specific "Process Time" was recorded;

"CB-F" is the concentration in ppmV of 2-chlorobutane intentionally added to the 2,5-DHF/helium vapor feed;

"CB-E" is the concentration in ppmV of 2-chlorobutane in the effluent vapor after passage through the 2-chlorobutane removal zone;

"CB Conv" is defined as 100 X [CB-F - CB-E]/CB-F; and

"DHF Conv" is defined as 100 X [DHF-F - DHF-E]/ DHF-F wherein DHF-F is the volume percent concentration of 2,5-DHF in the gas fed to the chloride removal zone and DHF-E is the concentration of 2,5-DHF in the gaseous effluent from the chloride removal zone. The amount of 2-chlorobutane in the vapor stream was determined by the in-line Electrolytic Conductivity Detector. The lower level of sensitivity of this detector was <1 ppmV in this mode of in-line gas phase analysis. The DHF Conv values indicate the mole percent of 2,5-DHF that was converted to other compounds, primarily 2,3-DHF, furan, and/or THF, all in very small amounts. The length of time at a particular reaction temperature can be determined by subtracting the final reaction time at a particular temperature from the initial reaction time at that particular temperature.

TABLE I

| Temp | GHSV | Process Time | CB-F | CB-E | CB CONV | DHF Conv |
|---|---|---|---|---|---|---|
| 122.6 | 1875 | 5.2 | 730 | 62.8 | 91.4 | 9.7 |
| 122.6 | 1874 | 5.9 | 730 | 104.4 | 85.7 | 5.3 |
| 155.6 | 400 | 14.2 | 750 | 94.5 | 87.4 | 0.2 |
| 155.6 | 395 | 25.2 | 750 | 384.0 | 48.8 | 0.2 |
| 155.4 | 390 | 47.8 | 640 | 484.5 | 24.3 | 0.0 |
| 155.4 | 395 | 48.4 | 550 | 427.4 | 22.3 | 0.0 |
| 182.0 | 395 | 49.5 | 550 | 0.0 | 100.0 | 0.1 |
| 182.0 | 395 | 56.8 | 550 | 156.2 | 71.6 | 0.5 |
| 182.7 | 380 | 69.8 | 450 | 178.2 | 60.4 | 0.3 |
| 215.5 | 375 | 71.2 | 450 | 0.0 | 100.0 | 1.6 |
| 215.2 | 375 | 76.6 | 450 | 0.0 | 100.0 | 2.1 |
| 215.4 | 380 | 79.9 | 750 | 20.3 | 97.3 | 2.1 |
| 215.7 | 385 | 99.3 | 750 | 20.3 | 97.3 | 1.4 |
| 243.8 | 395 | 101.3 | 750 | 0.0 | 100.0 | 7.8 |
| 244.3 | 395 | 103.5 | 750 | 0.0 | 100.0 | 8.2 |
| 244.5 | 395 | 126.3 | 720 | 0.0 | 100.0 | 8.3 |
| 215.5 | 400 | 126.3 | 720 | 98.6 | 86.3 | 3.4 |
| 214.5 | 400 | 150.7 | 720 | 180.0 | 75.0 | 2.0 |
| 215.6 | 400 | 170.3 | 720 | 205.9 | 71.4 | 1.2 |
| 215.1 | 410 | 178.1 | 750 | 292.5 | 61.0 | 1.3 |
| 214.8 | 410 | 220.1 | 750 | 249.8 | 66.7 | 1.4 |
| 215.6 | 410 | 243.2 | 500 | 155.0 | 69.0 | 1.3 |
| 215.0 | 410 | 246.8 | 770 | 262.8 | 65.9 | 2.3 |
| 214.6 | 410 | 266.8 | 770 | 253.3 | 67.1 | 1.3 |
| 214.3 | 410 | 274.2 | 770 | 305.7 | 60.3 | 1.0 |
| 215.8 | 410 | 294.1 | 800 | 316.0 | 60.5 | 1.9 |
| 214.4 | 410 | 321.7 | 600 | 225.0 | 62.5 | 1.5 |
| 214.2 | 410 | 342.1 | 500 | 181.5 | 63.7 | 1.1 |

The data in Table I indicate that the copper on silica material is a very effective copper-containing scavenger material for removing 2-chlorobutane from 2,5-DHF over a wide range of temperatures and for long, continuous periods of operation. Even though the copper on silica material may be referred to as a catalyst, it is actually a guard bed and is sacrificed during the course of operation. Thus, it becomes important that the copper-containing scavenger material have enough capacity for long periods of time to function as a practical 2-chlorobutane removal agent. The data in Table I show that increasing the reaction temperature of the copper-containing scavenger material increases the effectiveness and lifetime of operation. At a temperature of approximately 215° C., the activity remained essentially constant for 175 hours of operation, giving approximately 65% conversion, i.e., removal, of 2-chlorobutane. Because the activity was constant at the end of the experiment, it is apparent that satisfactory results could be obtained for longer times.

EXAMPLES 18

The procedure described in Example 17 was repeated using a fresh sample of the copper on silica catalyst material except that a vapor of 3,4-epoxy-1-butene was added to the material fed to the chloride removal zone. The EpB concentration was kept constant at 0.0032 mole, or volume percent, in the feed stream by flowing helium sweep gas through a separate liquid reservoir of EpB maintained at a constant temperature. Thus, the actual composition of the feed vapor stream was 18 mole % 2,5-DHF, 0.32 mole % EpB, 780–900 ppmV 2-chlorobutane, and the balance helium diluent. The results obtained from this experiment which was carried out over an extended period of time are shown in Table II wherein the terminology used has the meaning given to it above. The EpB vapor that was present in the feed was converted to crotonaldehyde at approximately 80% selectivity and to butadiene at approximately 20% selectivity. The formation of butadiene suggests that EpB results in the oxidation of copper to form copper oxide and butadiene. The presence of EpB in the feed vapor tests the capacity of the copper on silica scavenging material to remove 2-chlorobutane in the presence of an oxidizing agent such as EpB.

TABLE II

| Temp | GHSV | Process Time | CB-F | CB-E | CB CONV | DHF Conv |
|---|---|---|---|---|---|---|
| 123.0 | 410 | 19.1 | 890 | 489.5 | 45.0 | 0.2 |
| 122.8 | 410 | 22.9 | 890 | 776.1 | 12.8 | 0.0 |
| 145.3 | 410 | 24.7 | 900 | 701.1 | 22.1 | 0.0 |
| 163.8 | 410 | 25.3 | 900 | 465.3 | 48.3 | 0.0 |
| 168.2 | 410 | 41.2 | 900 | 684.0 | 24.0 | 0.0 |
| 196.0 | 400 | 42.7 | 900 | 540.0 | 40.0 | 0.2 |
| 196.0 | 400 | 44.6 | 900 | 473.4 | 47.4 | 0.3 |
| 196.0 | 400 | 46.0 | 900 | 513.0 | 43.0 | 0.2 |
| 217.4 | 400 | 47.3 | 900 | 123.3 | 86.3 | 0.9 |
| 215.0 | 400 | 50.7 | 900 | 57.6 | 93.6 | 1.0 |
| 216.0 | 400 | 63.9 | 900 | 234.0 | 74.0 | 0.0 |
| 216.0 | 400 | 66.3 | 900 | 414.0 | 54.0 | 0.1 |
| 215.8 | 400 | 72.5 | 780 | 433.7 | 44.4 | 1.0 |
| 215.2 | 400 | 89.5 | 780 | 428.2 | 45.1 | 1.1 |
| 216.0 | 400 | 94.3 | 780 | 499.2 | 36.0 | 0.1 |
| 215.8 | 400 | 120.5 | 780 | 502.3 | 35.6 | 0.9 |
| 215.9 | 400 | 142.5 | 780 | 473.5 | 39.3 | 0.8 |
| 244.9 | 400 | 170.2 | 780 | 325.3 | 58.3 | 2.3 |
| 245.2 | 400 | 186.7 | 780 | 159.1 | 79.6 | 4.2 |
| 244.1 | 400 | 191.6 | 780 | 217.6 | 72.1 | 3.5 |
| 244.2 | 400 | 210.3 | 780 | 228.5 | 70.7 | 2.8 |
| 244.4 | 400 | 216.7 | 780 | 225.4 | 71.1 | 3.2 |
| 244.1 | 400 | 232.7 | 780 | 185.6 | 76.2 | 2.2 |

The data in Table II show that stable, long term operation can be achieved even in the presence of vapor phase oxidizing species, such as 3,4-epoxy-1-butene. The efficiencies of 2-chlorobutane removal at 215° C. and 244° C. was approximately constant at 40–50% conversion and 70–80% conversion, respectively. This can be compared to performance in the absence of EpB at similar conditions (see Table I) in which the conversions of 2-chlorobutane at 215° C. and 244° C. were approximately 60–70% and 100%, respectively. Thus, even though performance efficiencies for 2-chlorobutane removal are somewhat lower in the presence of an oxidant such as EpB, the efficiency for removing 2-chlorobutane is quite high and suitable for long term, high activity operation. As in the case where no EpB was present, the conversion of 2,5-DHF to other products is negligible in all instances.

The invention has been described in detail with particular reference to preferred embodiments thereof, but it will be understood that variations and modifications can be effected within the spirit and scope of the invention.

We claim:

1. Process for the reduction of chloride content of a crude product stream comprising (i) furan, 2,3-dihydrofuran, 2,5-dihydrofuran, tetrahydrofuran or a mixture thereof and (ii) one or more organic chlorides selected from alkyl chlorides, alkenyl chlorides, cycloalkyl chlorides, aromatic chlorides, by the steps of:

(1) contacting the crude product stream with a copper-containing scavenger material in an organic chloride removal zone; and (2) removing from the chloride removal zone a refined product stream containing less chloride than the crude stream.

2. Process according to claim 1 wherein the organic chloride has the formula $RCl_x$ wherein R is a hydrocarbyl radical selected from the residues of an alkane, alkene, cycloalkane or carbocyclic, aromatic compound containing up to about 8 carbon atoms, x is 1 to 8 and the concentration of organic chloride in the crude product stream is about 50 to 2000 ppmV.

3. Process according to claim 2 wherein step (1) comprises contacting a vapor of the crude product stream with a copper-containing scavenger material at a temperature of about 100° to 260° C. in an organic chloride removal zone and the crude product stream contains about 50 to 2000 ppmV of an organic chloride selected from mono- and di-chlorides of alkanes of 2 to 6 carbon atoms.

* * * * *